United States Patent [19]

Hargis et al.

[11] 4,309,314

[45] Jan. 5, 1982

[54] CATALYTIC COMPOSITION FOR THE SELECTIVE FORMATION OF ETHANOL AND METHYL ACETATE FROM METHANOL AND SYNTHESIS GAS

[75] Inventors: Duane C. Hargis, Pleasant Ridge; Michael Dubeck, Birmingham, both of Mich.

[73] Assignee: Ethyl Corporation, Richmond, Va.

[21] Appl. No.: 153,610

[22] Filed: May 27, 1980

[51] Int. Cl.$^3$ .................... B01J 21/04; B01J 23/58; B01J 23/89

[52] U.S. Cl. ................... 252/466 B; 560/232; 568/902

[58] Field of Search ............. 252/466 B; 560/232; 568/902

[56] References Cited

U.S. PATENT DOCUMENTS 2,623,906 12/1952 Gresham ..................... 568/678
3,248,432 4/1966 Riley et al. .................. 568/902
3,285,948 11/1966 Butter ........................ 568/902
4,133,966 1/1979 Pretzer et al. ................ 568/902

FOREIGN PATENT DOCUMENTS 409501 4/1978 U.S.S.R. ..................... 585/487
422185 3/1978 U.S.S.R. ..................... 252/466 B

Primary Examiner—W. J. Shine
Attorney, Agent, or Firm—Donald L. Johnson; Joseph D. Odenweller; John F. Hunt

[57] ABSTRACT

A process for the selective formation of ethanol and methyl acetate by contacting methanol, hydrogen and carbon monoxide with a catalyst comprising rhodium and iron in the reduced state deposited on a support of alumina containing a minor amount of an alkaline metal at reaction conditions correlated so as to favor the formation of a substantial proportion of ethanol and methyl acetate.

5 Claims, No Drawings

CATALYTIC COMPOSITION FOR THE SELECTIVE FORMATION OF ETHANOL AND METHYL ACETATE FROM METHANOL AND SYNTHESIS GAS

BACKGROUND OF THE INVENTION

This invention concerns the selective preparation of ethanol and methyl acetate from methanol and synthesis gas. More particularly, the invention concerns the reaction of methanol and synthesis gas under heterogenous reaction conditions in the presence of a catalyst of rhodium and iron on alumina into which is diffused an alkaline metal compound to produce ethanol and methyl acetate.

The reaction of methanol with hydrogen and carbon monoxide to produce ethanol and other oxygen-containing organic compounds is known and disclosed in the prior art. For example, U.S. Pat. No. 4,133,966 discloses a process for the selective formation of ethanol which comprises contacting methanol, hydrogen and carbon monoxide with a catalyst system comprising cobalt acetylacetonate, a tertiary organo Group VA compound of the Periodic Table, a first promoter comprising an iodine compound and a second promoter compound comprising a ruthenium compound.

U.S. Pat. No. 3,285,948 entitled HALIDES OF RUTHENIUM AND OSMIUM IN CONJUNCTION WITH COBALT AND IODINE IN THE PRODUCTION OF ETHANOL FROM METHANOL, issued to Butter on Nov. 15, 1966, teaches a method for producing alcohols in which any source of cobalt soluble in the reaction medium which will yield a cobalt carbonyl or hydrogen cobalt carbonyl under the reaction conditions can be used. In addition, an iodine promoter is employed, for example, $I_2$, or alkali metal iodines. A secondary promoter is also employed, i.e., ruthenium halide or osmium halide. High selectivity is described as better when the secondary promoter is used in combination with the primary promoter and other reactants.

U.S. Pat. No. 4,013,700, entitled CATALYTIC PROCESS FOR POLYHYDRIC ALCOHOLS AND DERIVATIVES, issued to Cawse on Mar. 22, 1977, discloses a process for the preparation of polyhydric alcohols, their ether and ester derivatives, and oligomers of such alcohols. In particular, these alcohols and their derivatives are produced by reacting the oxides of carbon and hydrogen in the presence of a quaternary phosphonium cation and a rhodium carbonyl complex at elevated temperature and pressure.

Another process is set forth in U.S. Pat. No. 3,248,432, entitled PROCESS FOR THE PRODUCTION OF ETHYL ALCOHOL, issued to Riley et al on Apr. 26, 1966, which relates to a process for the production of ethyl alcohol by the interaction of methanol, carbon monoxide and hydrogen at elevated temperature and pressure in the presence of a cobalt catalyst and an iodine promoter. Examples of suitable cobalt sources are described as any water-soluble source of cobalt, for example, the cobalt carbonyls, the lower salts of alkanoate cobalt, such as cobalt acetate, cobalt formate, cobalt propionate, and the like.

U.S. Pat. No. 2,623,906, entitled PREPARATION OF ORGANIC HYDROXY-CONTAINING COMPOUNDS BY REACTING ALCOHOLS WITH CARBON MONOXIDE AND HYDROGEN, issued to Greshaw on June 16, 1948, relates to a procedure for synthesizing mono and poly functional oxygen-containing organic compounds by the reaction of alcohols, carbon monoxide and hydrogen. Catalysts described as suitable for use include various cobalt compounds, for example, cobalt carbonyl, cobalt carbonyl hydride, metallic cobalt, and organic and inorganic cobalt salts.

Dutch Pat. No. 760,6138 entitled PROCESS FOR THE FORMATION OF ETHANOL FROM METHANOL AND SYNTHESIS GAS, issued to Shell International Research on June 8, 1976, relates to a process for producing alcohols which utilizes any soluble cobalt source which can generate a cobalt carbonyl or hydrocarbonyl by reaction with the synthesis gas. For example, sources of cobalt suitable for use are cobalt iodide or cobalt metal from which ions can be generated in situ. Organic salts of cobalt such as cobalt acetate, formate, or propionate are described as especially good sources, an iodide or bromide promoter is also utilized. In addition, the use of a tertiary phosphine is described as affording improved selectivity to the formation of alcohols.

U.S. Application Ser. No. 437,141 filed Jan. 28, 1974, now abandoned discloses a process for manufacturing acetic acid, its lower alkyl esters, ethanol and lower alkyl aldehydes by contacting a reaction mixture of an oxide of carbon and hydrogen with a solid metal catalyst from the group of rhodium, ruthenium, cobalt, osmium, iridium and platinum. In one embodiment disclosed therein, methanol is co-fed with hydrogen and carbon monoxide over a supported rhodium catalyst with the reported result that productivities of the process were improved with the addition of methanol to the fed gas.

U.S. Application Ser. No. 541,660 filed Jan. 16, 1975, now abandoned, discloses a process for the selective preparation of ethanol by continuously contacting a synthesis gas reaction mixture containing hydrogen and carbon monoxide with a catalyst of rhodium and iron dispersed on a particulate support.

So far as applicant is aware, however, no process is provided for selectively preparing ethanol and methyl acetate by contacting a mixture of methanol, carbon monoxide and hydrogen with a heterogenous catalyst comprising rhodium and iron supported on an alumina support containing an alkaline metal. Unexpectedly, applicant has discovered that large amounts of ethanol and methyl acetate can be produced by contacting such a gaseous reaction mixture with the catalyst composition disclosed herein.

SUMMARY OF THE INVENTION

Briefly, in accordance with the invention, a process is provided for the reaction of methanol, carbon monoxide and hydrogen to prepare ethanol and methyl acetate by passing a mixture of methanol, carbon monoxide and hydrogen over rhodium and iron supported on alumina containing an alkaline metal compound under suitable reaction conditions.

DESCRIPTION OF THE PREFERRED EMBODIMENT

Thus, one embodiment of the present invention is a process for selectively producing ethanol and methyl acetate which comprises reacting methanol with carbon monoxide and hydrogen in the presence of a heterogenous catalyst comprising rhodium and iron in the reduced state deposited on a support of alumina impregnated with a minor amount of an alkaline metal at reaction conditions correlated so as to favor the formation of a substantial proportion of ethanol and methyl acetate.

The catalyst used in the practice of this invention is also believed novel and that its constituents differ from those of the prior art. Thus, another embodiment of the present invention is a catalyst for selectively converting methanol, carbon monoxide and hydrogen to ethanol and methyl acetate, said catalyst comprising rhodium and iron in the reduced state deposited on a support of alumina impregnated with a minor amount of an alkaline metal.

PROCESS DISCUSSION

The reaction is conducted at more or less conventional reactive conditions of temperature, pressure, gas composition, and space velocity so that conventional technology and equipment may be used. Over all, the reaction is conducted at reactive conditions of temperature, pressure, gas composition and space velocity which are correlated to achieve optimal selectivity for ethanol and methyl acetate. The reaction efficiency, or selectivity, to ethanol and methyl acetate is invariably at least about 40% and is usually between about 50% and 70%. Under preferred or optimum conditions it exceeds 70% and can reach 80% or more excluding carbon dioxide and dimethyl ether as products. Selectivity is defined herein as the percentage of carbon atoms converted from carbon monoxide and methanol to a specified compound or compounds other than carbon dioxide.

The reaction is exothermic with the thermodynamic equilibra and the kinetic reaction rates being governed by the reaction temperature. In general, the temperature can range from about 225° C. to about 300° C. The reaction temperature appears to be an important process variable affecting not only total productivity, but selectivity towards ethanol and methyl acetate. For example, when a catalyst containing approximately 3.3 weight percent rhodium, 5.6 weight percent iron and 1.15 weight percent sodium was contacted with methanol and synthesis gas at 250° C., with all other variables held essentially constant, total conversion was observed to be approximately 4.5%. When the reaction temperature was increased to 275° C., total conversion increased to almost 100%. However, selectivity for ethanol and methyl acetate production decreased from approximately 40% of the reaction product at 250° C. to almost zero (0.3%) at 275° C. This is demonstrated by Run Nos. 5 and 6 in Table 1 below. In general, the effect of increasing reaction temperature also appears to increase methane productivity as well as light hydrocarbon ($C_2$–$C_5$ paraffinic and olefinic hydrocarbons) production.

The reaction zone pressure is desirably within the range of about 50 psig to about 250 psig, with a pressure of approximately 220 psig being preferred.

The ratio of hydrogen to carbon monoxide in the synthesis gas may vary somewhat. Normally, the mole ratio of hydrogen to carbon monoxide is within the range of 2:1 to 1:2. Preferably, the mole ratio of hydrogen to carbon monoxide is 1:1. Methanol is added to the synthesis gas prior to introducing the gaseous reactant mixture into the reaction zone. Typically, a 1:1 mole ratio of methanol to carbon monoxide is used in the practice of the present process.

Conversion is conveniently achieved by employing a high space velocity correlated with other reaction variables (e.g. temperature, pressure, gas compsition, catalyst, etc.). Space velocity of from about 800 to about 2000 gas hourly space velocities (volumes of reactant gas at 0° C. and 760 mm mercury pressure, per volume of catalyst per hour) are generally employed. A preferred gas hourly space velocity is approximately 1200 GHSV.

THE CATALYST

The rhodium-iron-alkaline metal catalyst of the present invention is rhodium provided in combination with iron on a suitable alumina support which has been impregnated with an alkaline metal considered to be present as an oxide in the support lattice. Preferred metals are sodium and calcium. Catalyst preparation is typically effected by depositing rhodium and iron onto a high surface area alumina support and then impregnating the support with an alkaline metal compound, preferably the hydroxides, acetates, nitrates, carbonates or carboxylates of sodium or calcium which decompose to form the oxide.

In general, suitable support materials may include alpha alumina, beta alumina, gamma or eta alumina, aluminosilicates and magnesium silicates. Gamma alumina is preferred as the catalyst base or support.

The rhodium and iron may be deposited onto the base or support by any of the techniques commonly used for catalyst impregnation, as for example, impregnation from an organic or inorganic solution, precipitation, etc. Conveniently, a solution of a heat decomposable inorganic or organic rhodium compound and an iron compound is appropriately contacted with the support material and the support is then dried and heated, the latter advantageously under reducing conditions, to form a finely dispersed rhodium-iron containing catalyst. These materials may be deposited concurrently or sequentially. Illustrative of water-soluble compounds are the chloride and nitrate salts of rhodium and iron. In preparing the catalyst composition, the support material is contacted with just enough solution of rhodium and iron compounds to wet the support so that little or no excess solution is used. This technique which insures that the desired concentration of rhodium and iron will be incorporated into the catalyst composition is known in the art and is referred to as the incipient wetness technique. After impregnating the support material, the catalyst is subjected to drying conditions to lower the water content of the resultant composition to the lowest possible level. In a typical drying procedure, the impregnated support is slowly heated from room temperature up to a temperature of approximately 100° C. and is maintained at this temperature for at least one hour, preferably from 1 to 24 hours, until substantially all of the water is removed from the composition. The dried composition is then reduced with hydrogen. It has been found advantageous to reduce the catalyst composition by contacting the composition in a reduction zone with hydrogen at room temperature and then heating the catalyst reduction zone slowly from room temperature up to a temperature of about 400° C. Reduction is continued at this temperature for approximately 16 to 24 hours until both the rhodium and iron components are reduced to the zero valent state. It is not critical that reduction of the dried catalyst composition be initiated at room temperature. Alternatively, the dried catalyst can be placed in the reduction zone immediately after drying and reduction can commence at an elevated temperature, for example, 200° C. as illustrated in Example 1 below.

The alumina support onto which the rhodium and iron components of the catalyst composition have been deposited is then impregnated with an aqueous solution of an alkaline metal compound using the incipient wetness technique, aforedescribed. Typically, the rhodium-iron containing support is contacted with 3–5 milliliters of a solution of alkaline metal compound dissolved in distilled water in an amount sufficient to provide from about 0.1 to about 5.0 percent by weight of alkaline metal on the catalyst. Sodium hydroxide and calcium acetate have been found to be particularly effective alkaline metal compounds for use in the practice of the present invention. The effectiveness of sodium and calcium indicates that other alkaline metals selected from the alkaline metals in Groups I and II of the Periodic Table can also be used in the practice of the present process. Following adsorption of the alkaline metal compound dissolved in aqueous solution, the impregnated support material is dried by slowly heating the composition from room temperature up to a temperature of approximately 100° C. Heating at this temperature is continued for at least one hour and preferably longer, typically up to 24 hours, until substantially all of the water is removed from the composition. After drying, the composition is then reduced with hydrogen by contacting the composition in a reduction zone with hydrogen and slowly heating the reduction zone from room temperature up to approximately 300° C. The reduction zone is maintained at this temperature for approximately 16 to 24 hours in order to effect reduction of the final composition.

It is preferred that the catalyst contain from about 1.0 to about 10.0 weight percent rhodium and from about 1.0 to about 10.0 weight percent iron based on the total weight of the catalyst composition. The amount of alkaline metal in the composition should range from about 0.1 weight percent to about 5.0 weight percent based on the total weight of the composition. An especially effective catalyst composition has been found to comprise approximately 3.3 percent by weight rhodium metal and 5.6 precent by weight metallic iron on a gamma-alumina support impregnated with 2.0 percent by weight of sodium hydroxide (1.15 weight percent sodium). Another catalyst found to be particularly effective for converting methanol and synthesis gas to ethanol and methyl acetate comprises a composition containing approximately 3.3 percent by weight rhodium metal and 3.4 percent by weight iron on a gamma-alumina support impregnated with approximately 8.3 percent by weight calcium acetate (2.10 percent by weight calcium).

The bulk volume of a weighed catalyst sample is determined and the sample is placed in the test reactor (described below). The quantity of catalyst charged to the reactor is typically about 2 to 3 grams.

TEST REACTOR

The reactor used in the practice of the present invention was a stainless steel tube of 0.305 in. internal diameter, 0.375 in. outside wall diameter with a wall thickness of 0.035 in. The length was 14 inches and the reactor capacity was approximately 16.5 ml. The tube was packed with a catalyst prepared as described above supported on a glass wool support. Carbon monoxide and hydrogen were fed to the reactor in the desired mole ratio from 1750 psig headers. Approximately 2.0 to 3.0 grams of catalyst were placed in the reactor on the support. The reactor was then pressurized with hydrogen and the flow of carbon monoxide and hydrogen was adjusted to achieve the desired composition. During pressurization of the reactor, the reactor temperature and pressure were adjusted to reaction conditions. At least 5 to 6 hours were allowed for the reactor to come to a steady state before beginning to measure actual time of reaction. Methanol was then mixed with the carbon monoxide and hydrogen components of the gaseous reaction mixture in the desired mole ratio and the composite mixture was fed into the reaction zone of the reactor. The reaction was allowed to proceed for about 3 to 24 hours after which time a sample of liquid product was collected by cooling the product containing gas through a cold water condenser at approximately 225 psig and then trapping the liquid product in a dry-ice acetone trap having a capacity of approximately 55 cc. The liquid product from the trap and the condenser were then combined to obtain a single liquid sample which was analyzed by gas chromatography. The non-condensable gases were metered through a wet-test meter to determine the volume of gas, and a gas sample was collected to determine its composition.

The following examples serve to provide specific illustrations of the present invention.

EXAMPLE 1

This example illustrates the preparation of the preferred catalyst of the present invention.

A solution was prepared by dissolving 1.7384 grams of rhodium trichloride, $RhCl_3.3H_2O$, (obtained commercially from Alfa Products, 152 Andover Street, Danvers, Maine 01923) and 8.7320 grams of ferric nitrate, $Fe(NO_3)_3.9H_2O$ (obtained from the J. T. Baker Chemical Company, Phillipsburg, N.J. 08865) in distilled water to a final volume of 50 milliliters. The solution was heated until lukewarm to dissolve all of the salts so that the solution appeared homogeneous. The resultant aqueous solution was used to impregnate 22.5 grams of gamma-alumina (1.2 mm) obtained from Rhone-Poulenc Industries, Division Chimic Fine, 30340 Usine, De Salindres by adding the solution to the gamma-alumina support in a 250 milliliter suction flask. The support was submerged in the solution over the weekend. The support and solution were then poured into a crystallizing dish and heated over a hot plate set on the "Low" position for about 5 hours. The impregnated support was then dried in an oven at 100° C. overnight (approximately 17 hours). The composition was then placed in the tubular test reactor, aforedescribed, and reduced with hydrogen by flowing hydrogen over the composition for approximately 6 hours while slowly increasing the temperature in the reduction zone from 200° C. to about 400° C. The composition was then reduced overnight (for about 16 hours) at approximately 400° C. The resultant composition was a gamma-alumina supported catalyst containing approximately 3.3 weight percent rhodium and approximately 5.6 weight percent iron. Next, 3.28 grams of the catalyst was impregnated by the incipient wetness technique with 0.0656 grams of sodium hydroxide dissolved in 3 milliliters of distilled water to give a composition containing 1.15 weight percent of sodium. The composite composition was then dried in an oven at 100° C. for approximately 2 hours. Following this, the composition was reduced in hydrogen at 300° C. overnight.

The catalyst prepared by this procedure was used in the following reactions conducted in the tubular flow test reactor aforedescribed under the designated conditions to demonstrate the selectivity of the catalyst for producing ethanol and methyl acetate from methanol, carbon monoxide and hydrogen. T,0160

This example establishes that when temperature and pressure are carefully controlled and the catalyst employed is rhodium and iron supported on gamma-alumina having dispersed therein an alkaline metal that substantial amounts of ethanol and methyl acetate are produced with relatively low yields of light hydrocarbons. Reference to Table 1 shows that the combined ethanol-methyl acetate yield varied from about 40% to about 80%. The remaining products were primarily carbon dioxide and methane. Of the organic products formed in Run Nos. 3 and 12, ethanol and methyl acetate accounted for approximately 77% and 80% respectively of the products-excluding carbon dioxide and dimethyl ether as products. In both Run Nos. 3 and 12, ethanol was the major product. The specific activity of the catalyst is represented by a "turnover number" which is defined as the number of micromoles of product formed per gram of catalyst per minute. In Run Nos. 3 and 12 aforementioned, the ethanol turnover numbers were 44 and 26 $\mu$moles/g.-min., respectively.

In general, methane formation decreased when methanol was a co-reactant, sometimes by as much as one-half as demonstrated in Run Nos. 2 and 4. Reference to Run Nos. 6, 7 and 8 show that varying the $H_2/CO$ ratio between 0.5 and 2.0 seemed to have little effect on the oxygenated product yield. Lowering the space velocity by a factor of two also appeared to have little effect on oxygenated product yield as demonstrated by Run Nos. 11 and 14. Increasing the temperature to 275° C., however, had a dramatic effect on the selectivity of the catalyst. Reference to Run No. 5 shows that 99% of the carbon fed to the reaction zone was converted to methane and carbon dioxide when the reaction temperature was increased to 275° C.

EXAMPLE 2

This example illustrates the preparation of another preferred catalyst of the present invention.

A catalyst was prepared containing approximately 3.3% by weight rhodium metal and 3.4% by weight metallic iron supported on gamma-alumina according to the procedure set forth in preceding Example 1. The supported catalyst (3.28 grams) was then impregnated with 0.282 grams of $Ca(C_2H_3O_2)_2$ (obtained from the Baker and Adamson General Chemical Division of the Allied Chemical and Dye Corporation, New York, N.Y.) dissolved in 3 ml. of distilled water. The composition was dried in an oven at 100° C. for approximately 2 hours and then reduced in hydrogen at 300° C. overnight. The resultant catalyst composition contained approximately 3.3% by weight rhodium, 3.4% by weight iron and 2.1% by weight calcium.

The catalyst prepared by this procedure was used in the following reactions conducted in the tubular flow test reactor aforedescribed under the designated conditions.

TABLE 2

Methanol-Synthesis Gas Reaction over 8.3% $Ca(OAc)_2$-3.3% Rh-3.4% Fe/$\gamma$-$Al_2O_3$ Catalyst

| Run | 1 | 2 | 3 | 4 | 5 | 6 | 7 |
|---|---|---|---|---|---|---|---|
| $H_2/CO$ | 1.0 | 1.0 | 1.0 | 1.0 | 1.0 | 1.0 | 1.0 |
| Temp, °C | 250 | 275 | 275 | 275 | 275 | 275 | 275 |
| CO, moles/hr | .134 | .134 | .134 | .134 | .134 | .134 | .134 |
| MeOH, moles/hr | .134 | .119 | .020 | .111 | .120 | .127 | .126 |
| Pressure, psig | 220 | 220 | 220 | 220 | 220 | 220 | 220 |
| GHSV | 1800 | 1730 | 1290 | 1700 | 1740 | 1770 | 1760 |
| Time, hrs | 2.25 | 2.5 | 4.0 | 2.0 | 2.0 | 2.0 | 2.6 |
| C Conv, % | 2.6 | 3.2 | 3.0 | 3.0 | 2.8 | 2.8 | 2.3 |
| Production Dist., C% | | | | | | | |
| | | * | | * | | * | * | * | * | * | |
| $CO_2$ | 7.7 | | 10.5 | | 21.0 | | 20.3 | | 21.6 | | 23.4 | | 17.8 | |
| $CH_4$ | 3.7 | 4.1 | 6.0 | 6.9 | 30.9 | 40.2 | 16.2 | 21.1 | 15.9 | 21.4 | 19.3 | 26.8 | 13.8 | 18.0 |
| $C_2$-$C_5$ HC | 3.7 | 4.2 | 5.3 | 6.1 | 15.5 | 20.1 | 14.5 | 19.0 | 13.4 | 18.1 | 13.2 | 18.2 | 8.0 | |
| MeOH | | | | | | | | | | | | | | |
| $Me_2O$ | 2.9 | | 2.8 | | 2.1 | | 3.1 | | 4.2 | | 4.5 | | 5.2 | |
| EtOH | 43.3 | 48.4 | 46.5 | 53.6 | 22.1 | 28.8 | 29.8 | 38.9 | 30.7 | 41.4 | 24.5 | 34.0 | 31.6 | 41.0 |
| MeOAc | 33.4 | 37.3 | 21.8 | 25.2 | 4.8 | 6.3 | 10.5 | 13.7 | 11.1 | 14.9 | 10.7 | 14.8 | 16.6 | 21.5 |
| other oxygenates | 5.4 | 6.1 | 7.2 | 8.2 | 3.5 | 4.7 | 5.6 | 8.6 | 4.0 | 5.4 | 4.5 | 5.9 | 5.6 | 9.2 |
| Turnover No, umole/g-min. | | | | | | | |
| $CO_2$ | 2.98 | | 4.66 | | 6.19 | | 8.22 | | 8.34 | | 9.33 | | 5.84 | |
| $CH_4$ | 1.41 | | 2.65 | | 9.13 | | 6.55 | | 6.14 | | 7.72 | | 4.54 | |
| $C_2$-$C_5$ HC | .51 | | .94 | | 1.65 | | 1.99 | | 1.83 | | 1.80 | | .91 | |
| MeOH | | | | | | | | | | | | | | |
| $Me_2O$ | .56 | | .61 | | .31 | | .63 | | .82 | | .89 | | .86 | |
| EtOH | 8.34 | | 10.3 | | 3.27 | | 6.04 | | 5.93 | | 4.90 | | 5.19 | |
| MeOAc | 4.25 | | 3.23 | | .47 | | 1.42 | | 1.43 | | 1.42 | | 1.81 | |
| other oxygenates | .88 | | 1.18 | | .48 | | 1.18 | | .62 | | .68 | | 1.20 | |
| $H_2O$ | 92.3 | | 60.3 | | 15.8 | | 59.0 | | 42.5 | | 30.1 | | 30.8 | |

*Distribution excluding $CO_2$ and $Me_2O$

The table shows that at the conditions observed selectivity for ethanol and methyl acetate was about the same when calcium was substituted for sodium as the alkaline metal component of the catalyst. As shown in Table 2, the combined ethanol-methyl acetate yield varied from about 35% to about 87% excluding $CO_2$ and dimethyl ether as products. Carbon dioxide and light hydrocarbons were the primary remaining products.

We claim:

1. A catalyst composition for selectively converting methanol, carbon monoxide and hydrogen to ethanol and methyl acetate consisting essentially of rhodium and iron in the reduced state deposited on a support of alumina on which is deposited a minor amount of a metal selected from the group consisting of sodium and calcium.

2. The composition of claim 1 wherein said catalyst contains from about 1.0 to about 10.0 weight percent rhodium, from about 1.0 to about 10.0 weight percent iron; and from about 0.1 to about 5.0 weight percent of a metal selected from the group consisting of sodium and calcium, based on the total weight of the catalyst.

3. The composition of claim 2 wherein said metal is sodium.

4. The composition of claim 2 wherein said metal is calcium.

5. The composition of claim 1 wherein said support is selected from alpha alumina, gamma alumina and eta alumina.

UNITED STATES PATENT AND TRADEMARK OFFICE
CERTIFICATE OF CORRECTION

PATENT NO. : U.S. 4,309,314

DATED : January 5, 1982

INVENTOR(S) : Duane C. Hargis and Michael Dubeck

It is certified that error appears in the above-identified patent and that said Letters Patent are hereby corrected as shown below:

Column 7, line 6 after "hydrogen.", please delete "T,0160"

Column 7, after line 6, please insert the following 6 pages which when considered together form Table 1:

UNITED STATES PATENT AND TRADEMARK OFFICE
CERTIFICATE OF CORRECTION

PATENT NO. : U.S. 4,309,314  
DATED : January 5, 1982  
INVENTOR(S) : Duane C. Hargis and Michael Dubeck It is certified that error appears in the above-identified patent and that said Letters Patent are hereby corrected as shown below:

-- TABLE 1
Methanol-Synthesis Gas Reaction over 2% NaOH-3.3% Rh-5.6% Fe/$\gamma$-Al$_2$O$_3$ Catalyst

| Run | 1 | | 2 | |
|---|---|---|---|---|
| H$_2$/CO | 1.0 | | 1.0 | |
| CO, moles/hr | .110 | | .134 | |
| MeOH, moles/hr | .155 | | 0 | |
| Temp, °C | 250 | | 250 | |
| Time, hrs | 2.5 | | 17.1 | |
| Pressure, psig | 220 | | 220 | |
| GHSV | 1790 | | 1200 | |
| C Conv, % | 5.0 | | 7.1 | |
| Product Distribution, C% | | * | | * |
| CO$_2$ | 23.1 | | 11.4 | |
| CH$_4$ | 19.3 | 26.0 | 29.1 | 32.8 |
| C$_2$-C$_5$ HC | 5.3 | 7.1 | 7.4 | 8.4 |
| MeOH | | | 22.6 | 25.4 |
| Me$_2$O | 2.5 | | | |
| EtOH | 33.0 | 44.3 | 18.4 | 20.8 |
| MeOAc | 13.7 | 18.5 | 2.0 | 2.3 |
| other oxygenates | 3.1 | 4.2 | 8.8 | 9.8 |
| Turnover No, $\mu$mole/g-min | | | | |
| CO$_2$ | 15.4 | | 5.49 | |
| CH$_4$ | 12.9 | | 14.0 | |
| C$_2$-C$_5$ HC | 1.37 | | 1.29 | |
| MeOH | | | 10.9 | |
| Me$_2$O | .83 | | | |
| EtOH | 11.0 | | 4.44 | |
| MeOAc | 3.05 | | .32 | |
| other oxygenates | 1.70 | | 1.38 | |
| H$_2$O | 84.0 | | 12.9 | |

\* Distribution excluding CO$_2$ and Me$_2$O

UNITED STATES PATENT AND TRADEMARK OFFICE
CERTIFICATE OF CORRECTION

PATENT NO. : U.S. 4,309,314
DATED : January 5, 1982
INVENTOR(S) : Duane C. Hargis and Michael Dubeck It is certified that error appears in the above-identified patent and that said Letters Patent are hereby corrected as shown below:

| 3 | | 4 | | 5 |
|---|---|---|---|---|
| 1.0 | | 1.0 | | 1.0 |
| .134 | | .134 | | .134 |
| .156 | | .151 | | .153 |
| 250 | | 250 | | 275 |
| 2.5 | | 15.8 | | 2.3 |
| 220 | | 220 | | 220 |
| 1900 | | 1800 | | 1880 |
| 9.5 | | 3.2 | | 98.9 |
| | | | | |
| 8.3 | * | 27.7 | * | 37.3 |
| 6.1 | 6.7 | 15.1 | 21.9 | 58.6 |
| 2.1 | 2.3 | 7.1 | 10.3 | 3.7 |
| | | | | |
| 1.0 | | 3.7 | | |
| 63.7 | 70.2 | 26.8 | 39.0 | .3 |
| 9.0 | 10.0 | 15.6 | 22.7 | |
| 9.9 | 10.9 | 4.2 | 6.0 | .1 |
| | | | | |
| 11.5 | | 12.9 | | 538 |
| 8.43 | | 7.01 | | 844 |
| 1.04 | | 1.20 | | 23.7 |
| | | | | |
| .69 | | .86 | | .23 |
| 44.4 | | 6.24 | | 1.83 |
| 4.20 | | 2.42 | | .13 |
| 4.92 | | .83 | | .25 |
| 146 | | 19.7 | | 47.9 |

UNITED STATES PATENT AND TRADEMARK OFFICE
CERTIFICATE OF CORRECTION

PATENT NO. : U.S. 4,309,314

DATED : January 5, 1982

INVENTOR(S) : Duane C. Hargis and Michael Dubeck

It is certified that error appears in the above-identified patent and that said Letters Patent are hereby corrected as shown below:

TABLE 1 (continued)
Methanol-Synthesis Gas Reaction over 2% NaOH-3.3% Rh-5.6% Fe/$\gamma$-$Al_2O_3$ Catalyst

| Run | 6 | | 7 | | 8 | |
|---|---|---|---|---|---|---|
| $H_2/CO$ | 1.0 | | .50 | | 2.0 | |
| CO, moles/hr | .134 | | .179 | | .089 | |
| MeOH, moles/hr | .141 | | .142 | | .143 | |
| Temp, °C | 250 | | 250 | | 250 | |
| Time, hrs | 2.8 | | 2.5 | | 2.5 | |
| Pressure, psig | 220 | | 220 | | 220 | |
| GHSV | 1830 | | 1840 | | 1840 | |
| C Conv, % | 4.5 | | 3.1 | | 6.4 | |
| Product Distribution, C % | | | | | | |
| $CO_2$ | 27.1 | * | 29.8 | * | 23.4 | * |
| $CH_4$ | 17.6 | 22.6 | 16.4 | 24.7 | 31.0 | 41.0 |
| $C_2$-$C_5$ HC | 9.1 | 11.7 | 12.9 | 19.4 | 9.0 | 12.0 |
| MeOH | | | | | | |
| $Me_2O$ | 2.2 | | 3.5 | | 1.1 | |
| EtOH | 27.1 | 34.7 | 21.3 | 32.0 | 27.0 | 35.8 |
| MeOAc | 12.5 | 16.0 | 11.5 | 17.2 | 5.2 | 6.9 |
| other oxygenates | 4.5 | 5.9 | 4.9 | 7.3 | 3.2 | 4.3 |
| Turnover No, $\mu$mole/g-min. | | | | | | |
| $CO_2$ | 19.8 | | 15.0 | | 17.8 | |
| $CH_4$ | 12.9 | | 8.06 | | 23.5 | |
| $C_2$-$C_5$ HC | 2.40 | | 2.31 | | 2.60 | |
| MeOH | | | | | | |
| $Me_2O$ | .81 | | .88 | | .42 | |
| EtOH | 9.90 | | 5.35 | | 10.2 | |
| MeOAc | 3.04 | | 1.92 | | 1.32 | |
| other oxygenates | 1.35 | | .95 | | .90 | |
| $H_2O$ | 193 | | 56.9 | | 55.4 | |

* Distribution excluding $CO_2$ and $Me_2O$

UNITED STATES PATENT AND TRADEMARK OFFICE

CERTIFICATE OF CORRECTION

PATENT NO. : U.S. 4,309,314
DATED : January 5, 1982
INVENTOR(S) : Duane C. Hargis and Michael Dubeck It is certified that error appears in the above-identified patent and that said Letters Patent are hereby corrected as shown below:

| 9 | | 10 | | 11 | |
|---|---|---|---|---|---|
| 1.3 | | 1.3 | | 1.0 | |
| .134 | | .134 | | .134 | |
| 0 | | .138 | | .145 | |
| 250 | | 250 | | 250 | |
| 16.8 | | 2.5 | | 2.5 | |
| 220 | | 220 | | 220 | |
| 1200 | | 1990 | | 1850 | |
| 7.2 | | 5.3 | | 3.2 | |
| 11.8 | * | 16.3 | * | 18.9 | * |
| 38.8 | 44.0 | 15.9 | 19.4 | 15.7 | 20.0 |
| 8.7 | 9.9 | 5.5 | 6.7 | 7.2 | 9.1 |
| 5.2 | 5.9 | | | | |
| | | 1.6 | | 2.9 | |
| 26.7 | 30.2 | 41.8 | 50.9 | 29.2 | 37.4 |
| 1.3 | 1.4 | 13.4 | 16.3 | 18.8 | 24.0 |
| 7.4 | 8.4 | 5.6 | 6.6 | 7.5 | 9.4 |
| 5.77 | | 12.0 | | 8.52 | |
| 18.9 | | 11.7 | | 7.09 | |
| 1.62 | | 1.54 | | 1.20 | |
| 2.53 | | | | | |
| | | .58 | | .66 | |
| 6.50 | | 15.4 | | 6.61 | |
| .20 | | 3.29 | | 2.82 | |
| 1.16 | | 1.39 | | 1.13 | |
| 25.5 | | 72.0 | | 28.9 | |

UNITED STATES PATENT AND TRADEMARK OFFICE
CERTIFICATE OF CORRECTION

PATENT NO. : U.S. 4,309,314
DATED : January 5, 1982
INVENTOR(S) : Duane C. Hargis and Michael Dubeck It is certified that error appears in the above-identified patent and that said Letters Patent are hereby corrected as shown below:

TABLE 1 (continued)
Methanol-Synthesis Gas Reaction over 2% NaOH-3.3% Rh-5.6% Fe/γ-$Al_2O_3$ Catalyst

| Run | 12 | | 13 | | 14 | |
|---|---|---|---|---|---|---|
| $H_2$/CO | 1.0 | | 1.0 | | 1.0 | |
| CO, moles/hr | .067 | | .067 | | .067 | |
| MeOH, moles/hr | .108 | | .081 | | .041 | |
| Temp, °C | 250 | | 250 | | 250 | |
| Time, hrs | 2.5 | | 2.5 | | 2.0 | |
| Pressure, psig | 220 | | 220 | | 220 | |
| GHSV | 1080 | | 960 | | 780 | |
| C Conv, % | 10.0 | | 8.8 | | 11.7 | |
| Production Distribution, C% | | | | | | |
| $CO_2$ | 9.1 | * | 19.1 | * | 23.8 | * |
| $CH_4$ | 6.5 | 7.3 | 10.9 | 13.6 | 11.7 | 15.5 |
| $C_2$-$C_5$ HC | 3.2 | 3.5 | 4.3 | 5.5 | 5.3 | 7.0 |
| MeOH | | | | | | |
| $Me_2O$ | .9 | | 1.3 | | 1.0 | |
| EtOH | 59.0 | 65.5 | 39.6 | 49.7 | 34.4 | 45.7 |
| MeOAc | 10.1 | 11.2 | 16.0 | 20.1 | 15.3 | 20.4 |
| other oxygenates | 10.9 | 12.0 | 8.8 | 11.0 | 8.6 | 11.5 |
| Turnover No, μmole/g-min. | | | | | | |
| $CO_2$ | 8.05 | | 12.7 | | 15.2 | |
| $CH_4$ | 5.82 | | 7.20 | | 7.47 | |
| $C_2$-$C_5$ HC | 1.05 | | 1.11 | | 1.23 | |
| MeOH | | | | | | |
| $Me_2O$ | .38 | | .44 | | .31 | |
| EtOH | 26.3 | | 13.1 | | 11.0 | |
| MeOAc | 2.99 | | 3.54 | | 3.27 | |
| other oxygenates | 3.39 | | 1.73 | | 1.75 | |
| $H_2O$ | 97.4 | | 47.5 | | 52.3 | |

* Distribution excluding $CO_2$ and $Me_2O$

UNITED STATES PATENT AND TRADEMARK OFFICE
CERTIFICATE OF CORRECTION

PATENT NO. : U.S. 4,309,314

DATED : January 5, 1982

INVENTOR(S) : Duane C. Hargis and Michael Dubeck

It is certified that error appears in the above-identified patent and that said Letters Patent are hereby corrected as shown below:

| 15 | | 16 | | 17 | |
|---|---|---|---|---|---|
| 1.0 | | 1.0 | | 1.0 | |
| .067 | | .067 | | .133 | |
| .083 | | .086 | | .083 | |
| 250 | | 250 | | 250 | |
| 15.7 | | 3.0 | | 2.7 | |
| 220 | | 220 | | 220 | |
| 970 | | 980 | | 1570 | |
| 4.8 | | 4.6 | | 3.7 | |
| 31.9 | * | 36.5 | * | 30.1 | * |
| 16.3 | 26.2 | 16.2 | 26.8 | 19.7 | 29.6 |
| 9.8 | 15.7 | 9.4 | 15.6 | 12.1 | 18.2 |
| 3.0 | | 3.2 | | 3.2 | |
| 20.6 | 33.2 | 19.6 | 32.4 | 21.9 | 32.8 |
| 11.6 | 18.7 | 11.6 | 19.2 | 10.1 | 15.1 |
| 3.8 | 6.1 | 3.6 | 4.9 | 2.9 | 4.3 |
| 12.7 | | 12.9 | | 12.1 | |
| 5.93 | | 5.73 | | 7.95 | |
| 1.30 | | 1.23 | | 1.76 | |
| .55 | | .56 | | .64 | |
| 3.75 | | 3.47 | | 4.41 | |
| 1.41 | | 1.37 | | 1.35 | |
| .51 | | .48 | | .46 | |
| 1.48 | | 6.90 | | 11.4 | — — |

Signed and Sealed this

Eleventh Day of May 1982

[SEAL]

Attest:

GERALD J. MOSSINGHOFF

Attesting Officer

Commissioner of Patents and Trademarks